(12) United States Patent
Talish

(10) Patent No.: US 6,406,443 B1
(45) Date of Patent: Jun. 18, 2002

(54) SELF-CONTAINED ULTRASOUND APPLICATOR

(75) Inventor: Roger J. Talish, Hillsborough, NJ (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 09/592,703

(22) Filed: Jun. 13, 2000

Related U.S. Application Data

(60) Provisional application No. 60/139,125, filed on Jun. 14, 1999.

(51) Int. Cl.$^7$ ............................................... A61B 17/56
(52) U.S. Cl. ............................................. 601/2; 607/50
(58) Field of Search ................... 601/2, 3, 4; 600/437, 600/439; 607/50, 51, 151, 152

(56) References Cited

U.S. PATENT DOCUMENTS

| 4,530,360 | A | | 7/1985 | Duarte |
| 4,550,714 | A | * | 11/1985 | Talish et al. ................. 128/1.5 |
| 4,917,092 | A | | 4/1990 | Todd et al. |
| 5,003,965 | A | | 4/1991 | Talish et al. |
| 5,186,162 | A | | 2/1993 | Talish et al. |
| 5,211,160 | A | * | 5/1993 | Talish et al. ................... 128/24 |
| 5,314,401 | A | | 5/1994 | Tepper |
| 5,415,167 | A | | 5/1995 | Wilk |
| 5,520,612 | A | | 5/1996 | Winder et al. |
| 5,556,372 | A | | 9/1996 | Talish et al. |
| 5,626,554 | A | | 5/1997 | Ryaby et al. |
| 5,904,659 | A | * | 5/1999 | Duarte et al. ................... 601/2 |
| 6,165,144 | A | * | 12/2000 | Talish et al. ................... 601/2 |

* cited by examiner

Primary Examiner—Marvin M. Lateef
Assistant Examiner—Eleni Mantis Mercader
(74) Attorney, Agent, or Firm—Bruce D. Gray; Kristin L. Johnson; Kilpatrick Stockton LLP

(57) ABSTRACT

A self-contained ultrasound applicator for therapeutically treating injuries. The self-contained ultrasound applicator comprises a cantilever mounting structure, a cantilever connected to the mounting structure, a main operating unit operably mounted adjacent the cantilever and an ultrasonic transducer positioned adjacent a distal portion of the cantilever for abutment with a treatment site. The self-contained ultrasound applicator includes a means for attaching adjacent a treatment site. The cantilever is configured to urgingly bias the ultrasonic transducer toward a treatment site when mounted adjacent the treatment site.

11 Claims, 3 Drawing Sheets

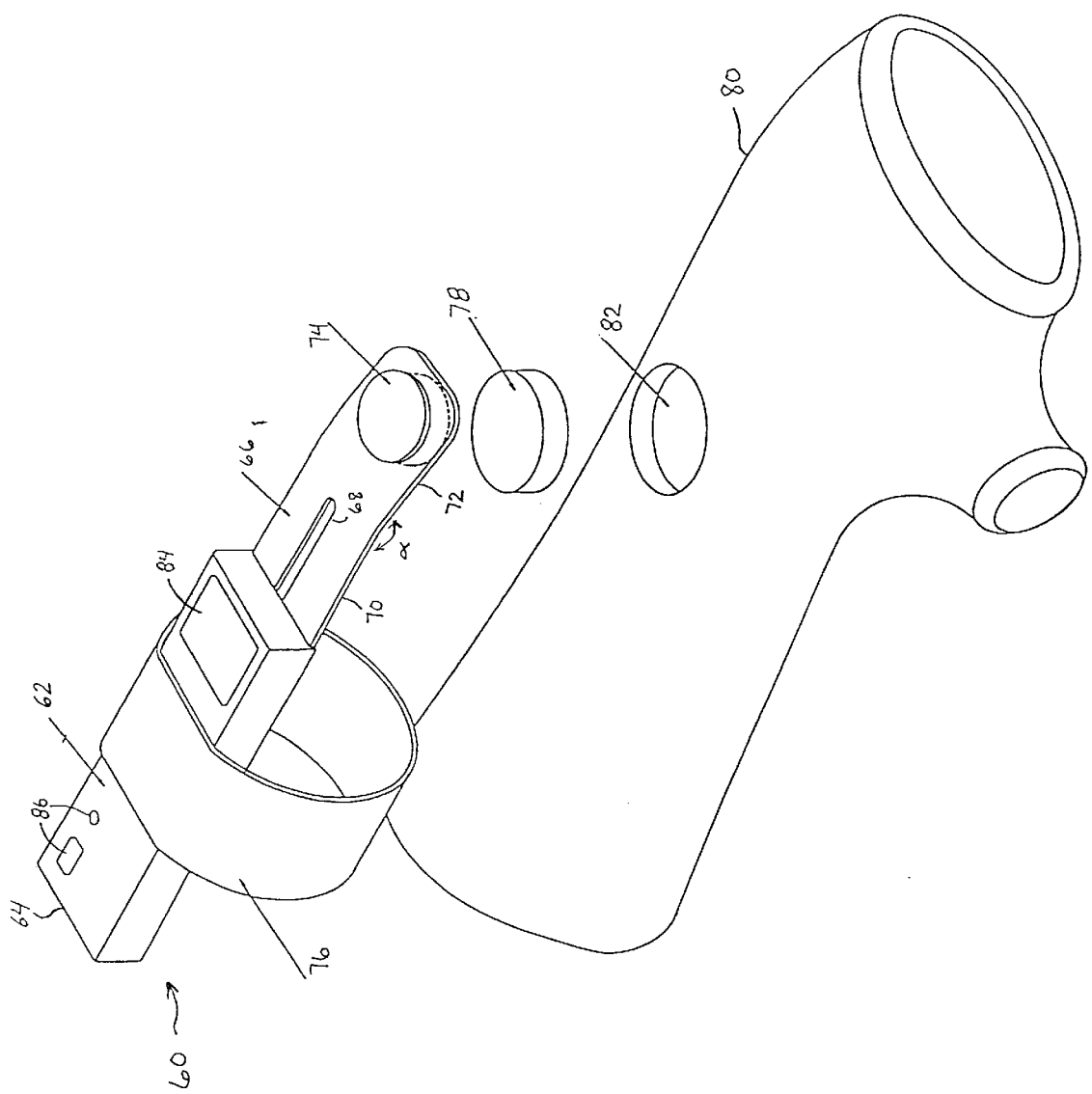

SELF-CONTAINED ULTRASOUND APPLICATOR

This application claims benefit of Provisional application 60/139,125 filed Jun. 14, 1999.

BACKGROUND OF THE INVENTION

1. Technical Field of the Invention

The present invention relates to an apparatus for therapeutically treating injuries using ultrasound. More particularly, the present invention relates to a self-contained ultrasound applicator which may be mounted on a patient to ultrasonically treat bone injuries, a variety of musculoskeletal injuries and other treatable injuries.

2. Description of the Related Art

The use of ultrasound to therapeutically treat and evaluate bone injuries is known. Impinging ultrasonic pulses having appropriate parameters, e.g., frequency, pulse repetition, and amplitude, for suitable periods of time and at a proper external location adjacent a bone injury has been determined to accelerate the natural healing of, for example, bone breaks and fractures. For patients with reduced healing capacity, such as elderly persons with osteoporosis, ultrasonic therapy may promote healing of bone injuries that would otherwise require prosthetic replacement or leave the patient permanently disabled.

U.S. Pat. No. 4,530,360 to Duarte describes a basic non-invasive therapeutic technique and apparatus for applying ultrasonic pulses from an operative surface placed on the skin at a location adjacent a bone injury. The applicator described in the '360 patent has a plastic tube which serves as a grip for the operator, an RF plug attached to the plastic tube for connection to an RF source, and internal cabling connected to an ultrasonic transducer. To apply the ultrasound pulses during treatment, an operator must manually hold the applicator in place until the treatment is complete. As a result, the patient is, in effect, immobilized during treatment. The longer the treatment period, the more the patient is inconvenienced. The '360 patent also describes a range of RF signals for creating the ultrasound, ultrasound power density levels, a range of duration for each ultrasonic pulse, and a range of ultrasonic pulse frequencies.

U.S. Pat. Nos. 5,003,965 and 5,186,162, both to Talish et al., relate to an ultrasonic body treatment system having a body-applicator unit connected to a remote control unit by sheathed fiber optic lines. The signals controlling the duration of ultrasonic pulses and the pulse repetition frequency are generated apart from the body-applicator unit. Talish et al. also describe a mounting fixture for attaching the body-applicator unit to a patient so that the operative surface is adjacent the skin location.

U.S. Pat. No. 5,556,372, also to Talish et al., attempts to improve upon the above ultrasonic body treatment systems by providing an ergonomically constructed ultrasonic transducer treatment head module. The main operating unit is constructed to fit within a pouch worn by the patient, while the transducer treatment head module is positioned adjacent the area of the injury. The apparatus described in the '372 patent therefore permits the patient to be mobile during treatment.

While the systems described in the above patents relate to therapeutic methods and apparatus for ultrasonically treating injured bone, they do not disclose a self-contained ultrasound applicator configured to urgingly bias the transducer toward a treatment site when mounted adjacent the treatment site.

It is therefore an objective of this invention to provide a self-contained ultrasound applicator which is configured to urgingly bias a transducer toward a treatment site when mounted adjacent thereto.

SUMMARY OF THE INVENTION

It is an object of the present invention to provide a self-contained ultrasound applicator having a main operating unit with an internal power source, a cantilever which is connected to and extends from the main operating unit, and an ultrasonic transducer which is connected adjacent a distal end of the cantilever. The self-contained ultrasound applicator is preferably provided with a means for attaching the applicator to a patient adjacent a treatment site. The applicator attaching means advantageously provides a patient with virtually unlimited mobility and comfort during treatment.

It is a further object of this invention to provide a self-contained ultrasound applicator having a cantilever which is configured to urgingly bias the transducer toward a treatment site when mounted adjacent the treatment site. The biasing feature of the cantilever configuration enhances the efficiency of the therapeutic treatment administered by the ultrasonic transducer.

These and other objects, features and advantages of the present invention will become apparent from the following detailed description of illustrative embodiments, which is to be read in connection with the accompanying drawings.

BRIEF DESCRIPTION OF THE DRAWINGS

For a better understanding of the invention, reference is made to the following description of exemplary embodiments thereof, and to the accompanying drawings wherein:

FIG. 5 is a perspective view of a self-contained ultrasound applicator in accordance with another embodiment of the present invention.

DETAILED DESCRIPTION OF A PREFERRED EMBODIMENT

Figure 1:
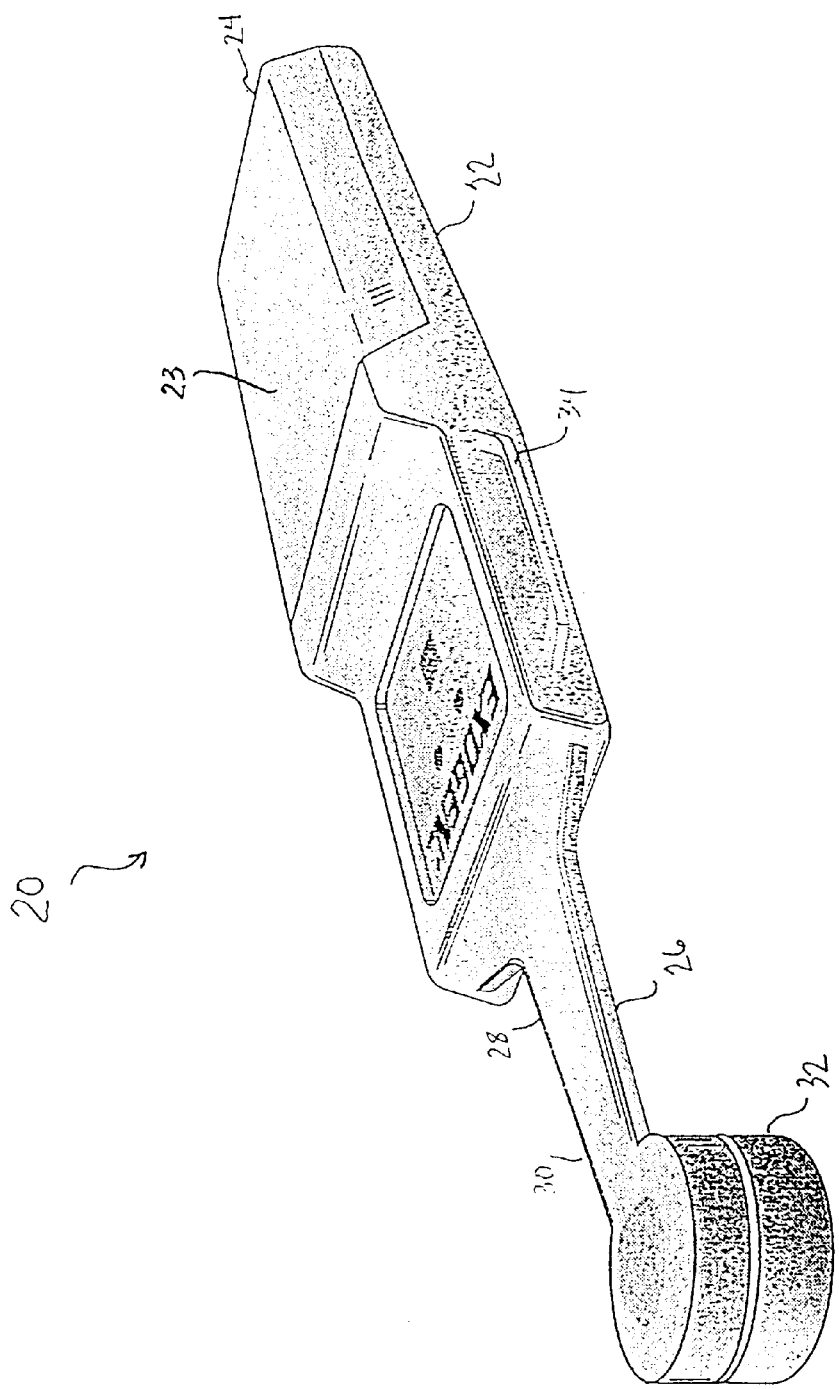
FIG. 1 is a perspective view of a self-contained ultrasound applicator in accordance with one embodiment of the present invention.

Referring initially to FIG. 1, there is shown a self-contained ultrasound applicator 20 in accordance with one embodiment of the present invention. The self-contained ultrasound applicator 20 comprises a main operating unit 22 on a proximal end 24 thereof. Main operating unit 22 includes a housing 23 which is typically constructed in two half-sections joined together by screws, ultrasonic welds or adhesives. Preferably, main operating unit 22 has an internal power source for powering signal generator circuitry in an ultrasonic transducer. The internal power source typically comprises at least one lithium battery positioned in a battery compartment.

Signal generator circuitry, within the signal generator, generates and controls the pulses transferred to an ultrasonic transducer assembly. Preferably, signal generator circuitry includes a processor having memory (e.g., RAM and ROM)

and stored programs (e.g., system and application) for controlling the operation of the processor, as well as the transducer treatment head module. A processor is typically coupled to a display and a keypad and is configured to receive data from the keypad and to transfer data to the display. The processor may include a microprocessor, such as the Intel® 80/x86 family of microprocessors, or the processor may be a microcontroller having internal memory. A commnunication interface may be connected between a communication port and the processor to communicate with, for example, an external computer. The communication interface may be a serial interface, such as an RS-232 interface, a parallel interface, or a modem.

The processor is also utilized to control the treatment sequence, i.e., the start time and the stop time of the ultrasonic treatment. The processor may be preprogramimed for treatment times and the user (e.g. the physician or patient) selects one of the treatment times via a keypad, or the processor may be programmed by the user via the keypad to set the start and stop sequence. Typical treatment times may range between 1 and 55 minutes, although treatments in the order of 10–20 minutes are common. Typical signal generator circuitry as is known to one of ordinary skill in the art may be used, for example, as disclosed in U.S. Pat. No. 5,556,372 to Talish et al.

A cantilever 26 is connected to, and extends from, main operating unit 22. Cantilever 26 has a proximal portion 28 and a distal portion 30. An ultrasonic transducer 32 is connected adjacent a distal portion 30 of cantilever 26.

It is known in the art that ultrasonic pulses attenuate rapidly in gases such as air, and that, consequently, the operative surface of the ultrasonic transducer must be as flush against the treatment site as possible. It is also known in the art that, since it is often not possible to press the operative surface completely flush against the treatment site, ultrasonically conductive coupling gel is used between the operative surface and the treatment site to ensure a continuous contact. To further enhance the continuity of contact between ultrasonic transducer 32 and a treatment site, cantilever 26 is configured to urgingly bias the transducer 32 toward the treatment site when the self-contained ultrasound applicator 20 is mounted adjacent the treatment site. Preferred configurations of cantilever 26 are described below.

Handles 34 are mounted on either side of the self-contained ultrasound applicator 20. Handles 34 are provided to connect a means for attaching applicator 20 adjacent a treatment site. Preferably, the means for attaching the self-contained ultrasound applicator 20 to a treatment site comprises an adjustable strap. The adjustable strap is preferably in two sections and has a hook and loop type fastening assembly, such as velcro, so that the two sections may be fastened together and quickly unfastened. Other quick release fastening techniques are also contemplated.

Figures 2, 3, 4:
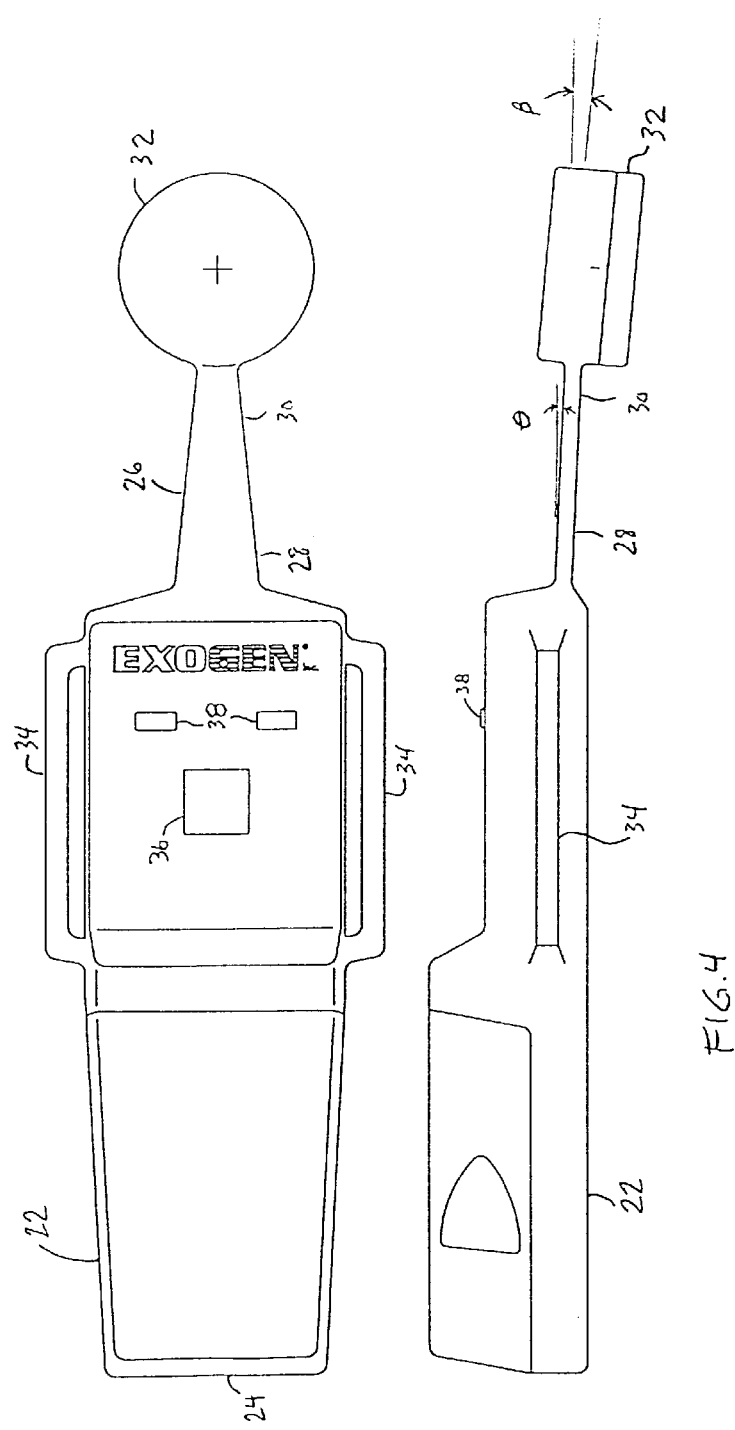
FIG. 2 is an end view of a self-contained ultrasound applicator.
FIG. 3 is a top view of a self-contained ultrasound applicator.
FIG. 4 is a side view of a self-contained ultrasound applicator.

FIGS. 2 and 3 illustrate end and top views of self-contained ultrasound applicator 20, respectively. Handles 34 are apparent on either side of self-contained ultrasound applicator 20. Cantilever 26 is shown extending substantially orthogonal to main operating unit 22. Main operating unit 22 further includes display 36 and keypads 38. Display 36 may be, for example, a liquid crystal type display or an LED type display suitable for displaying text and numerals. Display 36 and keypads 38 are operably connected to a printed circuit board located within main operating unit 22, as is known to one skilled in the art.

FIG. 4 is a side view of a self-contained ultrasound applicator which illustrates a downwardly projecting configuration of cantilever 26. As discussed supra, to function properly, the operative surface of the transducer 32 must be completely flush against a treatment site on a patient to eliminate any air gaps. The preferred configuration of cantilever 26 is designed to urgingly bias the operative surface of transducer 32 toward a treatment site, thereby enhancing the continuity of the contact area. As shown, cantilever 26 projects downward as it extends from main operating unit 22 to form a first predetermined angle $\Theta$ with a horizontal plane parallel to a bottom surface of the main operating unit 22. The magnitude of first predetermined angle $\Theta$ is typically in a range of about one degree to about fifteen degrees. A preferred magnitude of first predetermined angle $\Theta$ is two degrees. Also shown in FIG. 4 is a preferred configuration of transducer 32. Ultrasonic transducer 32 is connected to a distal portion 30 of cantilever 26. Moreover, in a preferred embodiment, ultrasonic transducer 32 tilts downward to form a second predetermined angle $\beta$ with a horizontal plane parallel to a bottom surface of main operating unit 22. The magnitude of second predetermined angle $\beta$, is typically in a range of about one degree to about twenty degrees. A preferred magnitude of second predetermined angle $\beta$ is five degrees.

Referring now to FIG. 5, there is shown a perspective view of another embodiment of a self-contained ultrasound applicator in accordance with the present invention. The self-contained ultrasound applicator 60 comprises a main operating unit 62 on a proximal end 64 thereof. Main operating unit 62 includes a housing which is typically constructed in two half-sections joined together by screws, ultrasonic welds or adhesives. Preferably, main operating unit 62 has an internal power source for powering signal generator circuitry in an ultrasonic transducer.

Main operating unit 62 also includes a display 84 and keypads 86. Display 84 may be, for example, a liquid crystal type display or an LED type display suitable for displaying text and numerals. Display 84 and keypads 86 are operably connected to a printed circuit board located within main operating unit 62, as is known to one skilled in the art.

A cantilever 66 is slidably connected, and extends from, main operating unit 62. In a preferred embodiment, a longitudinal slot 68 is provided in cantilever 66 for slidable engagement with main operating unit 62. Cantilever 66 has a proximal portion 70 and a distal portion 72. An ultrasonic transducer 74 is connected adjacent a distal portion 72 of cantilever 66.

A means for attaching self-contained ultrasound applicator 60 adjacent a treatment site is shown in a preferred embodiment comprising a strap 76. Strap 76 is preferably adjustable by means of a hook and loop type fastening assembly, such as Velcro, so that two sections of the strap may be fastened together and quickly unfastened. Other quick release fastening techniques are also contemplated.

As discussed above, it is known in the art that ultrasonic pulses attenuate rapidly in gases such as air, and that, consequently, the operative surface of the ultrasonic transducer must be as flush against the treatment site as possible. To enhance the performance of ultrasonic transducer 74, a gel pad 78 is typically provided and placed between ultrasonic transducer 74 and a treatment site. Gel pad 78 preferably contains an ultrasonically conductive coupling gel.

To enhance the contact between ultrasonic transducer 74 and gel pad 78, a distal portion 72 of cantilever 66 projects downward to form a predetermined angle $\alpha$. The downward projection of a distal portion 72 of cantilever 66 urgingly biases ultrasonic transducer 74 in a direction toward gel pad 78, thereby enhancing the continuity of a contact area therebetween. The magnitude of the predetermined angle α is typically in a range of about one degree to about twenty degrees.

During operation, a self-contained ultrasound applicator 60 is typically attached to a cast 80 of a patient by means of a strap 76. A cast 80 has a hole 82 to insertably receive a gel pad 78 and an ultrasonic transducer 74. Hole 82 is typically adjacent a treatment site corresponding to an injury on or in a patient's body. The distance between strap 76 and ultrasonic transducer 74 may be slidably adjusted along a longitudinal axis of slot 68 in cantilever 66, to ensure a proper fit between the self-contained ultrasound applicator 60 and a body of a patient by means of strap 76, and the proper contact between ultrasonic transducer 74 and gel pad 78 when insertably received in hole 82. Furthermore, the configuration of cantilever 66 forming predetermined angle α will urgingly bias ultrasonic transducer 74 toward gel pad 78 in hole 82 of cast 80.

Although the illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. For example, various shapes and configurations of the self-contained ultrasound applicator components are contemplated, as well as various types of construction materials. All such changes and modifications are intended to be included within the scope of the invention as defined by the appended claims.

What is claimed is:

1. A self-contained ultrasound applicator comprising:
   a main operating unit having an internal power source;
   a cantilever connected to, and extending from, said main operating unit; and
   an ultrasonic transducer connected adjacent a distal portion of said cantilever, said cantilever configured to urgingly bias the transducer toward a treatment site when mounted adjacent the treatment site.

2. A self-contained ultrasound applicator as recited in claim 1 further comprising a means for removably attaching said applicator to a patient adjacent a treatment site.

3. A self-contained ultrasound applicator as recited in claim 2 wherein said means for removably attaching said applicator comprises an adjustable strap.

4. A self-contained ultrasound applicator as recited in claim 1 having a cross-sectional profile wherein at least a portion of said cantilever projects downward as it extends from said main operating unit to form a first predetermined angle with a horizontal plane parallel to a bottom surface of said main operating unit to urgingly bias said transducer toward a treatment site.

5. A self-contained ultrasound applicator recited in claim 4 wherein said first predetermined angle formed by said downwardly projecting cantilever is in a range of about one degree to about fifteen degrees.

6. A self-contained ultrasound applicator as recited in claim 1 wherein said ultrasonic transducer tilts downward to form a second predetermined angle with a horizontal plane parallel to a bottom surface of said main operating unit to urgingly bias said transducer toward a treatment site.

7. A self-contained ultrasound applicator as recited in claim 6 wherein said second predetermined angle is in a range of about one degree to about twenty degrees.

8. A self-contained ultrasound applicator as recited in claim 1, wherein said cantilever is slidably connected to said main operating unit.

9. A self-contained ultrasound applicator comprising:
   a cantilever mounting structure removably positionable adjacent a treatment site;
   a cantilever connected to the mounting structure, said cantilever having a distal portion and a proximal portion;
   a main operating unit operably mounted adjacent the cantilever; and
   a transducer positioned adjacent the distal portion of the cantilever for abutment with a treatment site, said cantilever configured to urgingly bias the transducer toward a treatment site when mounted adjacent the treatment site.

10. A self-contained ultrasound applicator as recited in claim 9, wherein said main operating unit is positioned inside said cantilever mounting structure.

11. A method of therapeutically treating injuries using ultrasound comprising the steps of:
    mounting a self-contained ultrasound applicator, wherein the ultrasound applicator comprises a main operating unit, an ultrasonic transducer, and a cantilever extending between and connected to the main operating unit and the ultrasonic transducer, on a patent, thereby positioning the ultrasonic transducer adjacent a treatment site;
    adjusting an attachment member for said self-contained ultrasound applicator to urgingly bias said ultrasonic transducer toward a treatment site; and
    exciting said ultrasonic transducer for a predetermined period of time to effect treatment of an injury.

* * * * *